(12) United States Patent
Liu

(10) Patent No.: US 9,486,014 B2
(45) Date of Patent: *Nov. 8, 2016

(54) ELECTRONIC CIGARETTE

(71) Applicant: Qiuming Liu, Shenzhen (CN)

(72) Inventor: Qiuming Liu, Shenzhen (CN)

(73) Assignee: HUIZHOU KIMREE TECHNOLOGY CO., LTD., SHENZHEN BRANCH, Shenzhen, Guangdong Province (CN)

( * ) Notice: Subject to any disclaimer, the term of this patent is extended or adjusted under 35 U.S.C. 154(b) by 776 days.

This patent is subject to a terminal disclaimer.

(21) Appl. No.: 13/884,951

(22) PCT Filed: Feb. 5, 2013

(86) PCT No.: PCT/CN2013/071370
§ 371 (c)(1),
(2) Date: May 10, 2013

(87) PCT Pub. No.: WO2014/015669
PCT Pub. Date: Jan. 30, 2014

(65) Prior Publication Data
US 2014/0060528 A1 Mar. 6, 2014

(51) Int. Cl.
*A24F 47/00* (2006.01)
*A61M 15/06* (2006.01)
(52) U.S. Cl.
CPC ........... *A24F 47/008* (2013.01); *A24F 47/002* (2013.01); *A61M 15/06* (2013.01)
(58) Field of Classification Search
CPC .... A24F 47/00; A24F 47/002; A24F 47/004; A24F 47/006; A24F 47/008; A61M 15/06
See application file for complete search history.

(56) References Cited

U.S. PATENT DOCUMENTS

| | | | |
|---|---|---|---|
| 7,351,066 B2* | 4/2008 | DiFonzo | H01R 13/641 439/39 |
| 9,080,734 B2* | 7/2015 | Andersen | F21L 4/00 |
| 2005/0255718 A1* | 11/2005 | McLeish | H01R 13/6205 439/39 |
| 2007/0178771 A1* | 8/2007 | Goetz | H01R 13/2428 439/669 |
| 2013/0152922 A1* | 6/2013 | Benassayag | A61M 15/06 128/202.21 |
| 2013/0220315 A1* | 8/2013 | Conley | A61M 11/042 128/202.21 |
| 2013/0255702 A1* | 10/2013 | Griffith, Jr. | A24F 47/008 131/328 |

* cited by examiner

*Primary Examiner* — Anthony Calandra
(74) *Attorney, Agent, or Firm* — Cheng-Ju Chiang

(57) ABSTRACT

An electronic cigarette includes an absorption stem and a power source stem; the absorption stem has a first and second absorption stem electrodes contained therein; the power source stem has a first and second power source stem electrodes contained therein; when the absorption stem and power source stem are connected with each other, the first absorption stem electrode is electrically connected to the first power source stem electrode, while the second absorption stem electrode is electrically connected to the second power source stem electrode. The absorption stem and power source stem are connected together by magnetic force absorption. The power source stem and absorption stem of the electronic cigarette of the present invention are connected with each other by means of magnetic force absorption, thus leading to easy assembling and disassembling, simple construction, easy repair and replacement, good electrical contact, and long lifetime.

17 Claims, 10 Drawing Sheets

ELECTRONIC CIGARETTE

CROSS REFERENCE TO RELATED APPLICATIONS

The present application is a 35 U.S.C. §371 National Phase conversion of International (PCT) Patent Application No. PCT/CN2013/071370, filed on Feb. 5, 2013, the disclosure of which is incorporated by reference herein. The PCT International Patent Application was filed in Chinese.

FIELD OF THE INVENTION

The present invention relates to technical field of electronic cigarette and more particularly, relates to an electronic cigarette of which connection is realized by magnetic force absorption.

BACKGROUND OF THE INVENTION

With more concerns given to people health, people have been aware of damages of tobacco to body health and as a result, electronic cigarette appears. For an electronic cigarette, cigar liquid is atomized by the atomizer such that the user can smoke. During formation process of cigar liquid, hazardous substance such as nicotine and tar is removed from cigar liquid; damage to user's body health is greatly decreased. Also, as no hazardous substance such as nicotine and tar is contained in cigar liquid, using of the electronic cigarette will gradually reduce reliance of user on traditional cigarette. Therefore, electronic cigarette may also assist in getting rid of smoking.

In general, an electronic cigarette includes an absorption stem and a power source stem. A cigar liquid cup for storage of cigar liquid and an atomizer for atomizing cigar into smoke are disposed in the absorption stem. A battery for supplying power to the atomizer is contained in the power source stem. For a conventional electronic cigarette, the absorption stem and power source stem are connected with each other by screwing. This kind of connection will result in time consumption and inconvenience during assembling and disassembling process. In addition, the internal construction of the absorption stem is complex thus leading to inconvenience in maintenance and replacement of the atomizer. Moreover, using of the screwing connection will result in misalignment between the electrode of the power source stem and that of the absorption stem due to bias between the electrodes during contact of the electrodes. Too tight or too loose screwing will both easily result in misalignment. After a period of use, the misalignment will become serious and, bad contact between the electrodes will be caused and accordingly, the atomizer will not work normally.

Therefore, there is need for providing an electronic cigarette which is easy to be assembled and disassembled, has simple construction, easy to be repaired and replaced, has good electrical contact, and has long lifetime.

SUMMARY OF THE INVENTION

The object of the invention is to provide an electronic cigarette which is easy to be assembled and disassembled and has simple construction.

To realize the above object, the following technical solution is proposed. The invention provides an electronic cigarette including an absorption stem and a power source stem. The absorption stem has a first and second absorption stem electrodes contained therein. The power source stem has a first and second power source stem electrodes contained therein. When the absorption stem and power source stem are connected with each other, the first absorption stem electrode is electrically connected to the first power source stem electrode, while the second absorption stem electrode is electrically connected to the second power source stem electrode. The absorption stem and power source stem are connected together by magnetic force absorption. In the present invention, the absorption stem and power source stem are connected together by magnetic force absorption and therefore, it has simple construction, is easy to be assembled and disassembled, and is easy to be maintained and replaced.

Furthermore, a magnetic absorption element is disposed in at least one of the connection end of the absorption stem and connection end of the power source stem. The connection end of the absorption stem is provided with a metal absorption stem connection member, while the connection end of the power source stem is provided with a metal power source stem connection member. The absorption stem connection member and power source stem connection member are detachably connected with each other, and they are engaged with each other by absorption force of the magnetic absorption element.

The magnetic absorption element may take various forms and in some embodiments, it may be permanent magnet. The absorption stem connection member and power source stem connection member are attracted together and are pressed against the top end of the permanent magnet.

Furthermore, the permanent magnet is held in the absorption stem connection end or power source stem connection end by a metal holding sleeve. The metal holding sleeve may be made of conductive material such as iron and copper.

Moreover, the permanent magnet is disposed on the power source stem connection end and a fixation hole is defined in the permanent magnet. The first power source stem electrode is received in the fixation hole of the permanent magnet. An insulation member is disposed between the permanent magnet and the first power source stem electrode. The power source stem connection member is the second power source stem electrode, and the absorption stem connection member is the second absorption stem electrode. The first absorption stem electrode is placed in the absorption stem connection member. An insulation member is disposed between the first and second absorption stem electrodes.

Moreover, the holding sleeve is of a circular cup and includes a side wall, a bottom wall and a cavity defined by the side wall and bottom wall together. The holding sleeve is pressed against and secured on an inner wall of the power source stem connection end by its side wall. A locating step is formed on inner side of the inner wall of the holding sleeve for supporting the permanent magnet. The permanent magnet is installed in the cavity of the holding sleeve and the bottom of the permanent magnet is supported on the locating step. One end of the power source stem connection member and one end of the absorption stem connection member are inserted into the holding sleeve and pressed against the top end of the permanent magnet such that the permanent magnet is held in place. A through hole is defined in the bottom wall of the holding sleeve through which the first power source stem electrode passes.

Preferably, the power source stem connection member is pressed against and secured on the power source stem connection end by the holding sleeve and, the holding sleeve is pressed against and secured on the inner wall of the power source stem connection end. The permanent magnet is held in the holding sleeve.

Furthermore, the power source stem connection member includes a first connection portion of cylinder in which a first cavity is formed for insertion with the absorption stem connection member. A locating step, which is radially outwardly extended from an outer wall of the first connection portion and used for engaging with the power source stem connection end, is provided on the outer wall of the first connection portion. The power source stem connection member is pressed against and secured on the inner wall of the power source stem connection end by the outer wall of the first connection portion. Using the above structure, the power source stem connection member is simply coupled with the absorption stem connection member.

In some embodiments, the power source stem connection member further includes a second connection portion for insertion with the absorption stem connection end. The second connection portion extends axially upon the locating step away from the first connection portion such that a cylinder is formed. The first and second connection portions communicate with each other. A second cavity is defined in the second connection portion for containing the absorption stem connection end. The inner wall of the second connection portion is interference-fitted with the outer wall of the absorption stem connection end. This structure enhances connection reliability between the absorption stem and power source stem, makes connection easy and, produces good electrical contact between the electrodes of the absorption stem and power source stem.

Preferably, the absorption stem connection member includes an upper portion and a lower portion both of which are of a cylindrical shape. The upper portion is intended for connection with the absorption stem connection end, whereas the lower portion is intended for connection with the power source stem connection member. A locating step, which is extended outwardly and is pressed against the absorption stem connection end, is formed between the upper and power portions. The locating step also functions to be pressed against the power source stem connection member so as to realize location limiting purpose. A locking ring for mounting the first absorption stem electrode is formed on the inner wall of the lower portion. The first absorption stem electrode is secured in the locking ring by an insulation member. A venting hole is defined in the middle portion of the first absorption stem electrode. The outer wall of the upper portion of the absorption stem connection member is pressed against and inserted into the inner wall of the absorption stem connection end. The power portion of the absorption stem connection member is inserted into the power source stem connection member for engaging the same. This construction makes the absorption stem connection end and power source stem connection end be connected more tightly.

Preferably, the first power source stem electrode is of a cylindrical shape. A circular locating step is formed on the middle circumferential surface of the first power source stem electrode and said locating step divides the first power source stem electrode into an upper portion and a lower portion. In addition, an axially extended venting hole is defined in the first power source stem electrode.

Preferably, the insulation member is sleeved on the first power source stem electrode and, the first power source stem electrode and insulation member are inserted into the fixation hole of the permanent magnet and are locked therein. The bottom portion of the insulation member is pressed against the top portion of the locating step such that the locating step of the first power source stem electrode is located below the bottom portion of the permanent magnet and is isolated from the permanent magnet.

Moreover, an insulation washer is disposed between the first power source stem electrode and holding sleeve. An axially extended venting hole is defined in the middle portion of the insulation washer. The lower portion of the first power source stem electrode passes through the venting hole of the insulation washer and through hole of the holding sleeve and then extends out of the bottom wall of the holding sleeve. The insulation washer isolates the first power source stem electrode from the holding sleeve.

Further, a resilient member is sleeved on the lower portion of the first power source stem electrode. The two ends of the resilient member are respectively pressed against the locating step of the first power source stem electrode and insulation washer. The first power source stem electrode, permanent magnet, power source stem connection member and holding sleeve are engaged each other tightly due to pretension generated by compression of the resilient member. In addition, the resilient member makes the permanent magnet be pressed more tightly against both of the power source stem connection member and absorption stem connection member, thus leading to more stable connection structure, tighter physical and electrical contact between the first power source stem electrode and the first absorption stem electrode. Generally, the resilient member is a spring.

As an alternative embodiment, the permanent magnet may also be disposed at the absorption stem connection end. The fixation hole of the permanent magnet receives the first absorption stem electrode. An insulation member is provided between the permanent magnet and first absorption stem electrode. The absorption stem connection member is the second absorption stem electrode, while the power source stem connection member is the second power source stem electrode. The first power source stem electrode is disposed at the middle portion of the power source stem connection member. An insulation member is disposed between the first and second power source stem electrodes. The substantial features of this embodiment are consistent with those of the above-mentioned embodiment and therefore, no further description will be provided hereinafter.

As an alternative embodiment, in addition to the permanent magnet, the magnetic absorption element may also be made of electromagnetic coil assembly. The absorption stem connection member and power source stem connection member are attracted together and are pressed against the top end of the electromagnetic coil assembly.

Furthermore, the electromagnetic coil assembly is secured in the absorption stem connection end or power source stem connection end by a base.

In some embodiments, the electromagnetic coil assembly is placed inside the power source stem connection end and the electromagnetic coil assembly includes a magnetic core and a coil enwound on the magnetic core. A through hole is defined in the magnetic core. A groove is defined in the outer wall of the magnetic core for enwinding the coil thereon. A radially extended locating step is defined in the upper end of the magnetic core. The first power source stem electrode is inserted into the through hole of the magnetic core. An insulation sleeve is located between the magnetic core and first power source stem electrode. The power source stem connection member is used as the second power source stem electrode.

Further, the insulation sleeve is of a cylindrical shape. A circular locating step is formed on the middle circumferential surface of the insulation sleeve and said locating step divides the insulation sleeve into an upper portion and a lower portion. In addition, an axially extended venting hole is defined in the insulation sleeve. A receiving chamber is defined in the lower portion of the insulation sleeve for communicating with the through hole. The first power source stem electrode is inserted into the through hole of the insulation sleeve. The locating step of the insulation sleeve is located between the electromagnetic coil assemble and base and isolates them from each other.

Preferably, the first power source stem electrode is of a cylindrical shape. A circular locating step is formed on the middle circumferential surface of the first power source stem electrode and said locating step divides the first power source stem electrode into an upper portion and a lower portion. In addition, an axially extended venting hole is defined in the first power source stem electrode. The insulation sleeve is sleeved on the first power source stem electrode and, the first power source stem electrode and insulation sleeve are inserted into the through hole of the electromagnetic coil assembly and are locked therein. The lower portion of the first power source stem electrode is received into the receiving chamber of the lower portion of the insulation sleeve. The locating step of the first power source stem electrode is pressed against the bottom end of the upper portion of the insulation sleeve.

Preferably, the base is of a circular cup and includes a side wall, a bottom wall and a cavity defined by the side wall and bottom wall together. The base is pressed against and secured on an inner wall of the power source stem connection end by its outer wall. A locating step is inwardly formed on the upper end of the side wall of the base. A through hole is defined in the bottom wall of the base through which the first power source stem electrode passes.

Preferably, an axially extended semi-circular stopping wall is formed on the bottom wall of the base around the through hole. The stopping wall separates an electric wire for connecting with the first power source stem electrode from another electric wire for connecting with the power source stem connection member.

Furthermore, a resilient member is sleeved on the lower portion of the first power source stem electrode. The two ends of the resilient member are respectively pressed against the locating step of the first power source stem electrode and inner side of the bottom wall of the base. The first power source stem electrode, permanent magnet, power source stem connection member and base are engaged each other tightly due to pre-tension generated by compression of the resilient member. In addition, the resilient member makes the electromagnetic coil assembly be pressed more tightly against both of the power source stem connection member and absorption stem connection member, thus leading to more stable connection structure, tighter physical and electrical contact between the first power source stem electrode and the first absorption stem electrode. Generally, the resilient member is a spring.

Moreover, the power source stem connection member is of a cylindrical shape and, a locating step extended radially outwardly is formed on the upper end thereof for engaging the power source stem connection end. The side wall of the power source stem connection member is divided into an upper portion for receiving the absorption stem connection member and a lower portion for receiving the electromagnetic coil assembly, the first power source stem electrode and base. The transition location between the upper portion and lower portion of the side wall of the power source stem connection member is provided with a step against which the upper end surface of the magnetic core of the electromagnetic coil assembly is pressed.

Preferably, the outer diameter of the upper portion of the side wall of the power source stem connection member becomes gradually greater such that the power source stem connection member is secured into the inner wall of the power source stem connection end. The lower end of the power source stem connection member is provided with two wiring pins for wiring.

Preferably, the absorption stem connection member includes an upper portion and a lower portion both of which are of a cylindrical shape. The upper portion is intended for connection with the absorption stem connection end, whereas the lower portion is intended for connection with the power source stem connection member. A locating step, which is extended radially outwardly and is pressed against the absorption stem connection end, is formed between the upper and power portions. The locating step also functions to be pressed against the power source stem connection member so as to realize location limiting purpose. A locking ring for mounting the first absorption stem electrode is formed on the inner wall of the lower portion. The first absorption stem electrode is secured in the locking ring by an insulation member. A venting hole is defined in the middle portion of the first absorption stem electrode.

Furthermore, the insulation ring is disposed between the first absorption stem electrode and locking ring of the absorption stem connection member. One end of the insulation ring is provided with inverted rim to be located at one side of the locking ring, while the other end thereof is provided with radially extended cylindrical boss to be located at the other side of the locking ring, hereby the insulation ring being just locked in the locking ring of the absorption stem connection member.

As an alternative embodiment, the electromagnetic coil assembly may also be placed inside the absorption stem connection end and the electromagnetic coil assembly includes a magnetic core and a coil enwound on the magnetic core. A through hole is defined in the magnetic core. A groove is defined in the outer wall of the magnetic core for enwinding the coil thereon. A radially extended locating step is defined in the upper end of the magnetic core. The first absorption stem electrode is inserted into the through hole of the magnetic core. An insulation sleeve is located between the magnetic core and first absorption stem electrode. The absorption stem connection member is used as the second absorption stem electrode. The substantial features of this embodiment are consistent with those of the above-mentioned embodiment and therefore, no further description will be provided hereinafter.

Compared with prior art, the invention has the following advantages: the power source stem and absorption stem of the electronic cigarette of the present invention are connected with each other by means of magnetic force absorption, thus leading to easy assembling and disassembling, simple construction, easy repair and replacement, good electrical contact, and long lifetime.

DETAILED DESCRIPTION OF THE INVENTION

Figure 1:
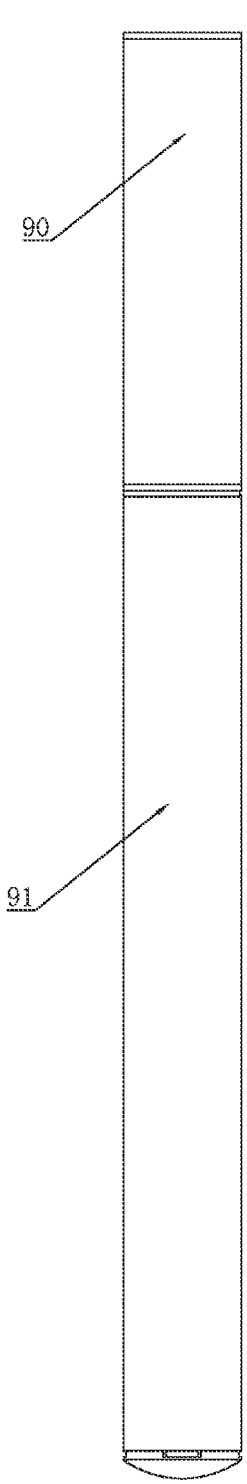
FIG. 1 shows a front view of an electronic cigarette according to a first embodiment of the invention.

Referring to FIGS. 1-11 showing a schematic view of the electronic cigarette according to a first embodiment, the electronic cigarette includes an absorption stem 90 and a power source stem 91 which are connected with each other by magnetic force. The absorption stem has a first and second absorption stem electrodes contained therein, while the power source stem has a first and second power source stem electrodes contained therein. When the absorption stem and power source stem are connected with each other, the first absorption stem electrode is electrically connected to the first power source stem electrode, while the second absorption stem electrode is electrically connected to the second power source stem electrode.

A magnetic absorption element is disposed in at least one of the connection end of the absorption stem 90 and connection end of the power source stem 91 engaged with the connection end of the stem 91. In one embodiment, the magnetic absorption element may be permanent magnet. The absorption stem connection member and power source stem connection member are attracted together and are pressed against the top end of the permanent magnet 8. The connection end of the absorption stem 90 is provided with a metal absorption stem connection member 5, while the connection end of the power source stem 91 is provided with a metal power source stem connection member 911. In one embodiment, the absorption stem connection member 5 and power source stem connection member 911 are made of iron. The absorption stem connection member 5 and power source stem connection member 911 are detachably connected with each other, and they are engaged with each other by absorption force of the magnetic absorption element 8.

The permanent magnet 8 is held in the power source stem connection member 911 by an iron holding sleeve 914. The permanent magnet 8 is of an annular shape and a fixation hole is defined in its middle portion. The first power source stem electrode 915 is received in the fixation hole of the permanent magnet 8. A power source stem insulation member 916 is disposed between the permanent magnet 8 and first power source stem electrode 915. The power source stem connection member 911 is used as the second power source stem electrode.

The absorption stem connection member 5 is the second absorption stem electrode. The middle portion of the absorption stem connection member 5 is provided with the first absorption stem electrode 13. An absorption stem insulation member 14 is disposed between the first absorption stem electrode 13 and the second absorption stem electrode.

The power source stem connection member 911 and absorption stem connection member 5 may each be stand-alone component independent of power source stem 91 or absorption stem 90. They may also be integral with the power source stem 91 or absorption stem 90. The holding sleeve 914 may also be stand-alone component independent of the power source stem 91, or may be integral with the power source stem 91.

In present embodiment, the absorption stem 90 includes an absorption sleeve 1, an atomization device 2, a cigar liquid cup 3, a nozzle case 4 and an absorption stem connection member 5 for connecting with the power source stem 91. The nozzle case 4 and absorption stem connection member 5 are mounted at two ends of the absorption sleeve 1 respectively. The atomization device 2 and cigar liquid cup 3 are installed in the absorption sleeve 1.

Figure 2:
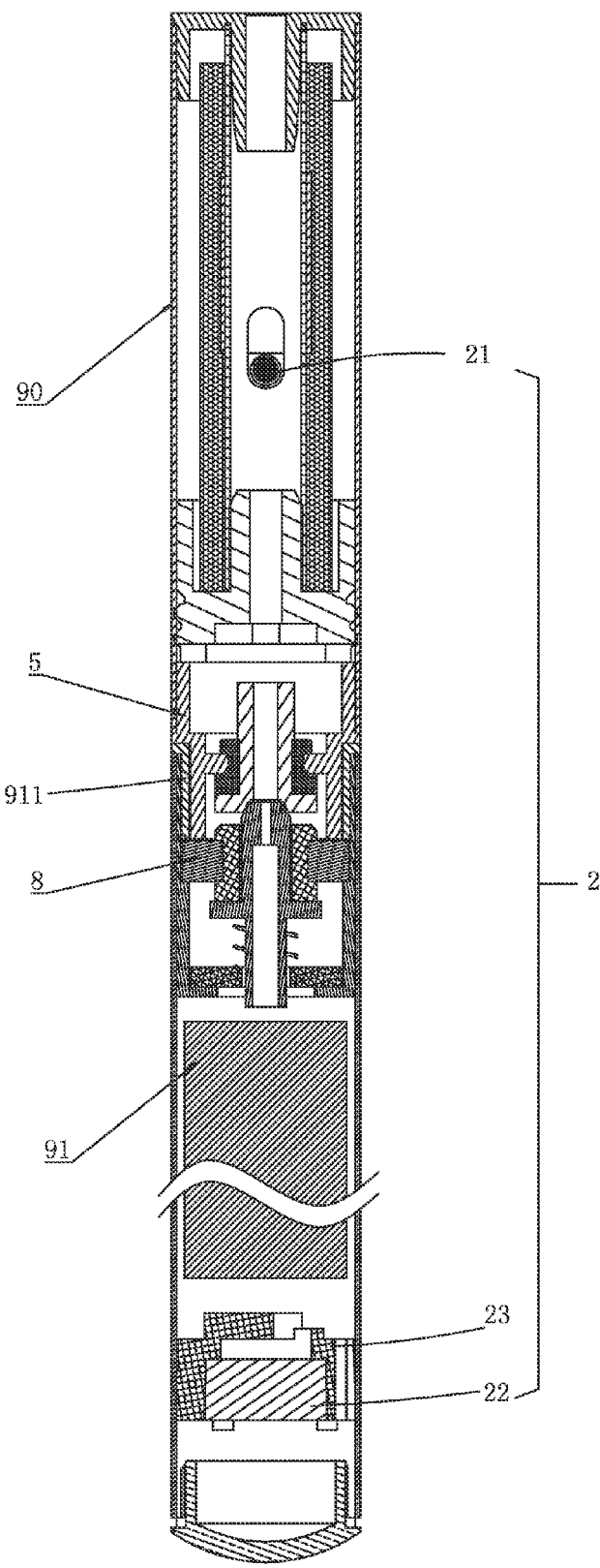
FIG. 2 shows a cross-sectional view of an electronic cigarette according to a first embodiment of the invention.
Figure 3:
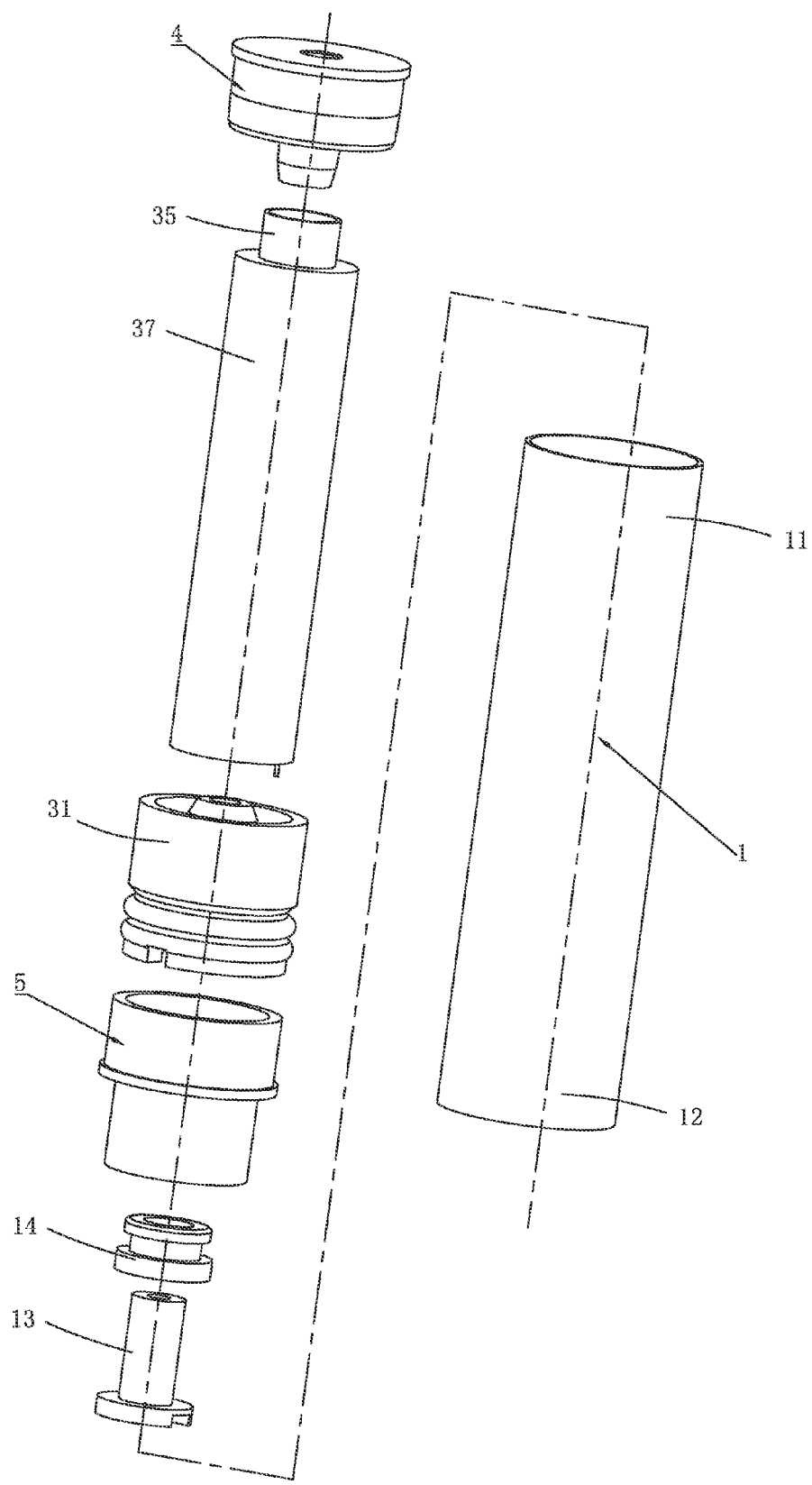
FIG. 3 shows an exploded view of an absorption stem of an electronic cigarette according to a first embodiment of the invention.

The absorption sleeve 1 is of a hollow cylindrical construction and is made of transparent or semitransparent plastic material or made of metal enclosure. As shown in FIGS. 2 and 3, the absorption sleeve 1 includes a first end 11 for placement of the nozzle case 4 and a second end 12 for placement of the absorption stem connection member 5. The first absorption stem electrode 13 and absorption stem insulation ring 14 are received in the absorption stem connection member 5 located on the second end 12. A venting hole is defined in the middle portion of the first absorption stem electrode 13.

As shown in FIGS. 2-6, the atomization device 2 includes an atomizer 21, an atomizer control circuit board 22 and a circuit board holding base 23 for accommodating and holding the atomizer control circuit board 22. The atomizer 21 is placed in the absorption sleeve 1, while the atomizer control circuit board 22 and circuit board holding base 23 are placed in the power source stem 91. The atomizer control circuit board 22 is provided with a mini pneumatic switch for control conduction of the electric circuit such that the atomizer 21 starts to work.

As shown in FIG. 3, the atomizer 21 is intended to change cigar liquid into smoke and it includes an electric heater coil 211 and a fiber member 212 for supporting the electric heater coil 211 and absorbing cigar liquid. The electric heater coil 211 is enwound on the fiber member 212. The fiber member 212 works like sponge so as to absorb and store cigar liquid, and may be made of material with good liquid absorption and storage ability such as glass fiber or cotton thread. The fiber member 212 is contained and secured in the cigar liquid cup 3. The two ends of the electric heater coil 211 pass through the cigar liquid cup 3 and then are connected with the two electrodes inside the power source stem 91.

Figure 4:
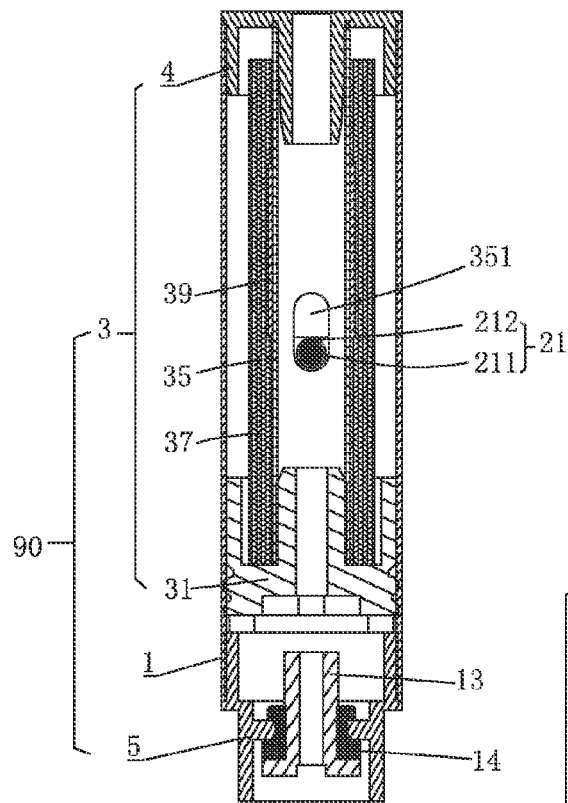
FIG. 4 shows an exploded view of an absorption stem of an electronic cigarette according to a first embodiment of the invention.

As shown in FIGS. 3-4, the cigar liquid cup 3 includes a cup base 31, a guiding tube 35, a liquid storage component 37, a locating tube 39 and the above-mentioned nozzle case 4. The cup base 31 and nozzle case 4 are disposed opposite to each other, distanced from each other, and are held in the inner wall of the absorption sleeve. The guiding tube 35 is held between the cup base 31 and nozzle case 4. The liquid storage component 37 is secured on the periphery of the guiding tube 35 and is disposed between the cup base 31 and nozzle case 4. The locating tube 39 is sleeved on the outer wall of the guiding tube 35 and is pressed against the atomizer 21 for preventing axial movement of the atomizer 21.

Figure 8:
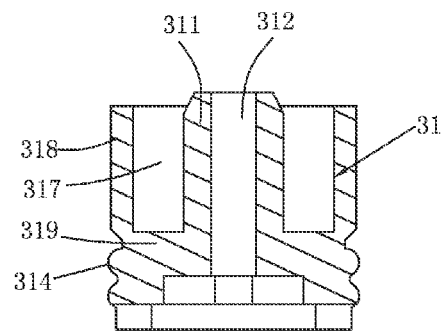
FIG. 8 shows a cross-sectional view of a cigar liquid cup base of an electronic cigarette according to a first embodiment of the invention.

As shown in FIG. 8, the cup base 31 is of a cylindrical cup construction and includes an annular side wall 318 and a circular cup bottom 319, a locating post 311 axially extended from the middle portion of the cup bottom 319. Herein, an annular cavity 317 is defined between the annular side wall 318 and locating post 311. A cup bottom venting hole 312 is defined which extends axially through the locating post 311 and cup bottom 319. Two wire guiding holes (not shown) are defined in the cup bottom 319 for passing the electric heater coil 211. An expansion ring 314 is disposed on the outer side of the side wall 318 for pressing against the absorption sleeve 1. The cup base 31 is pressed against and secured in the inner wall of the absorption sleeve 1 by its side wall 318 and expansion ring 314.

Figure 7:
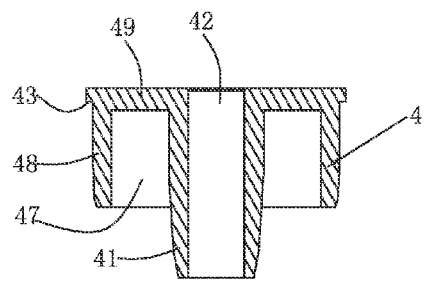
FIG. 7 shows a cross-sectional view of a nozzle case of an electronic cigarette according to a first embodiment of the invention.

The nozzle case 4 may be formed of silica gel, and its shape and size are consistent with the inner wall of the absorption sleeve 1. As shown in FIG. 7, the nozzle case 4 may take on cylindrical cover body, and includes an annular side wall 48, a top wall 48 and a locating post 41 axially extended from the middle portion of the top wall 49. An annular cavity 47 is defined by the locating post 41 and side wall 48. The nozzle case 4 further includes a nozzle case venting hole 42 axially extending through the locating post 41 and top wall 49, and a locating step 43 radially outwardly extended and matched with the first end 11 of the absorption sleeve 1. The outer diameter of the nozzle case 4 is slightly larger than the inner diameter of the absorption sleeve 1. The nozzle case 4 is pressed against and secured on the inner wall of the absorption sleeve 1 by its side wall 48. When the cigar liquid inside the cigar liquid cup 3 gives out, cigar liquid may be added into the cigar liquid cup 3 after the nozzle case 4 is removed. The locating post 41 of the nozzle case 4 is corresponding to the locating post 311 of the cup base 31, while the annular cavity 47 of the nozzle case 4 is corresponding to the annular cavity 317 of the cup base 31, for receiving respectively the two ends of the guiding tube 35 and two ends of the liquid storage component 37.

As shown in FIG. 4, the guiding tube 35 is used to support the liquid storage component 37 and, it is also used to control height of the cigar liquid cup 3 and support the fiber member 212. In addition, it is also used as a path for conducting smoke generated by atomization of cigar liquid by the atomizer 21 out of the absorption sleeve 1. The guiding tube 35 is a hollow circular tube and is made of plastic or fiber material such as a glass fiber tube. The guiding tube 35 includes an upper portion and a lower portion. The upper portion of the guiding tube 35 is sleeved on the locating post 41 of the nozzle case 4 and is sealably connected with the circumference of the locating post 41 of the nozzle case 4. The lower portion of the guiding tube is sleeved on the locating post 311 of the cup base 31 and is sealably connected with the circumference thereof. A holding groove 351 is defined in the guiding tube 35 and extends through its tube wall for supporting and securing the fiber member 212. The fiber member 212 transverses the two ends of the guiding tube 35, passes through the holding groove 351 and contacts the liquid storage component 37 so as to absorb cigar liquid which will be atomized by the electric heater coil 211.

Referring to FIGS. 3 and 4, the liquid storage component 37 serves to absorb and stores cigar liquid injected into the cigar liquid cup 3 such that the liquid later will be atomized by the atomizer 21. The liquid storage component 37 works like sponge so as to absorb and store cigar liquid, and may be made of material with good liquid absorption and isolation ability such as cotton material. The liquid storage component 37 is of a hollow cylindrical construction and is sleeved on the outside of the guiding tube 35 and is pressed against and supported on the outer wall of the guiding tube 35. The two ends of the liquid storage component 37 are inserted into the annular cavity 317 of the cup base 31 and annular cavity 47 of the nozzle case 4 respectively. The side wall of the liquid storage component 37 is pressed against the fiber member 212. Cigar liquid soaks into the fiber member 212 from the liquid storage component 37 and then is absorbed and finally vaporized by the electric heater coil 211 thus producing smoke.

As shown in FIG. 3, the locating tube 39 is used to limit location of the atomizer 21 on a guide rail 35. The locating tube 39 is a hollow insulated circular tube matched with the guiding tube 35, and may be made of plastic or fiber material such as glass fiber tube. The locating tube 39 is sleeved on the outer wall of the guiding tube 35. Interference fit exists between the locating tube 39 and guiding tube 35. The bottom end of the locating tube 35 is pressed against the atomizer 21 so as to prevent axial displacement of the atomizer 21 along the guiding tube 35.

Figure 9:
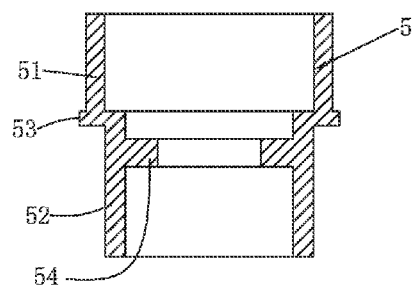
FIG. 9 shows a cross-sectional view of an absorption stem connection member of an electronic cigarette according to a first embodiment of the invention.

As shown in FIGS. 3, 4 and 9, the absorption stem connection member 5 is located at the second end 12 of the absorption sleeve 1 and its shape corresponds to the absorption sleeve 1, and is made of magnetic material such as iron. The absorption stem connection member 5 is inserted into the absorption sleeve 1 and contacts the cup base 31. The absorption stem connection member 5 is substantially of a hollow cylinder, and includes a cylindrical upper portion 51 and a cylindrical lower portion 52. The upper portion 51 is intended for connection with the absorption stem connection end (i.e., the second end 12 of the absorption sleeve 1), whilst the lower portion 52 is intended for connection with the power source stem connection member. A radially outwardly extended locating step 53 is formed between the upper portion 51 and lower portion 52 for contacting the absorption stem connection end. The locating step 53 also functions to be pressed against the power source stem connection member for purpose of limiting position. A locking ring 54 for mounting the first absorption stem electrode 13 is formed on the inner wall of the lower portion 52. The first absorption stem electrode 13 is held in the locking ring 54 by the absorption stem insulation member 14. A venting hole is defined in the middle portion of the first absorption stem electrode 13. The outer wall of the upper portion 51 of the absorption stem connection member 5 is inserted into and pressed against the inner wall of the absorption stem connection end. The lower portion 52 of the absorption stem connection member is inserted into the power source stem connection member. This construction makes the absorption stem connection end and power source stem connection end engage with each other tightly.

Figure 5:
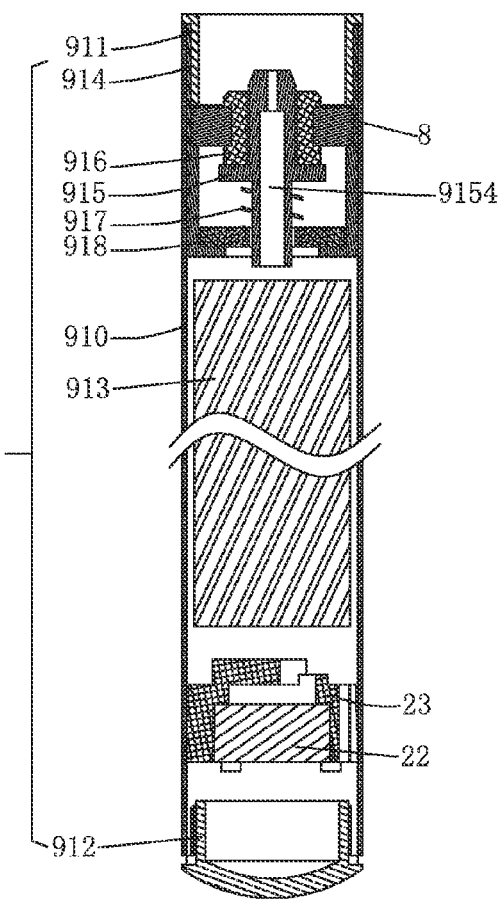
FIG. 5 shows a cross-sectional view of a power source stem of an electronic cigarette according to a first embodiment of the invention.
Figure 6:
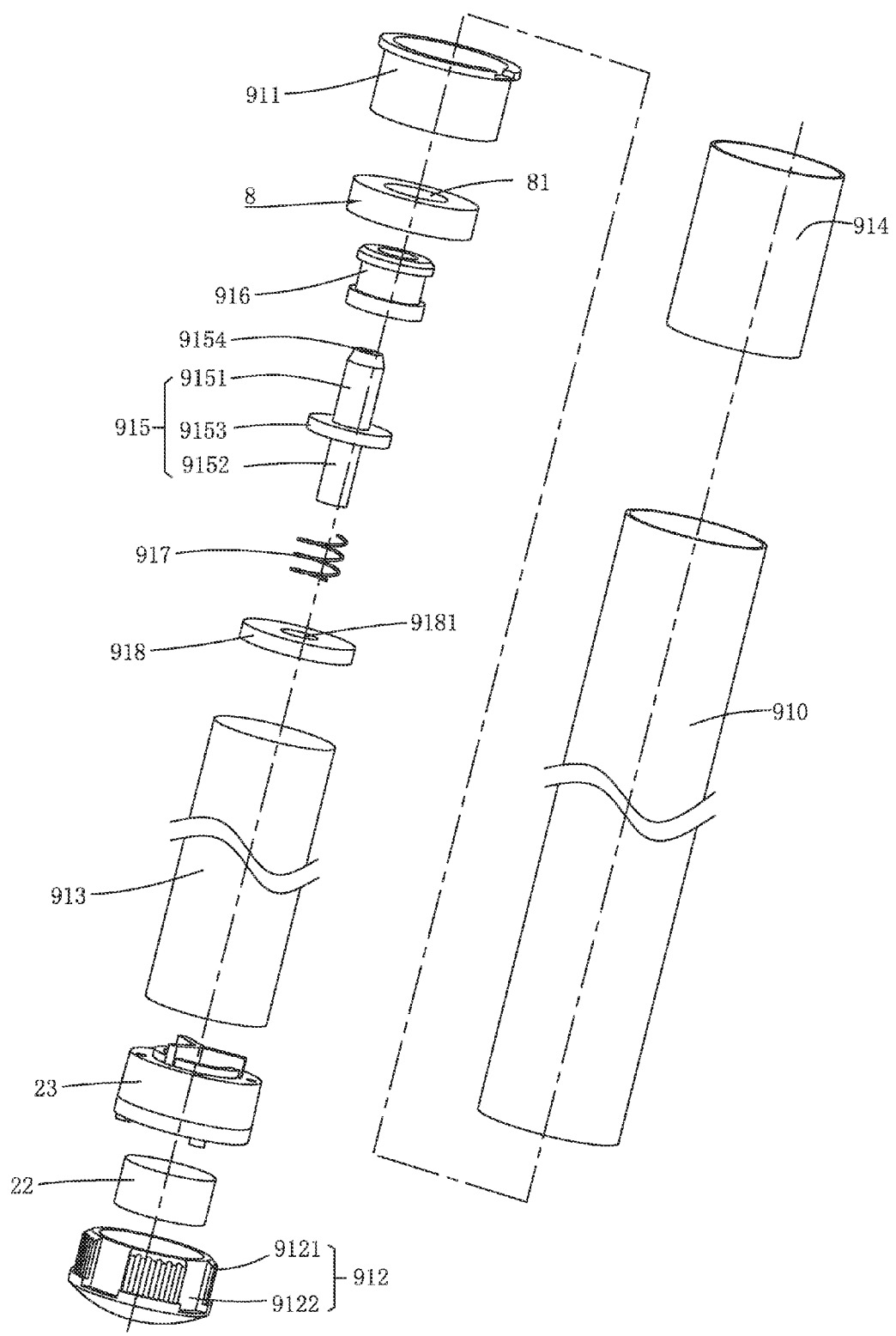
FIG. 6 shows an exploded view of a power source stem of an electronic cigarette according to a first embodiment of the invention.

Referring to FIGS. 5 and 6, the power source stem 91 includes a sleeve 910, a power source stem connection member 911 and a base cover 912 which are disposed at two ends of the sleeve 910 respectively, a battery 913 received in the sleeve 910, a holding sleeve 914 for holding the power source stem connection member 911 into the sleeve 910 and a first power source stem electrode 915 electrically connected with an electrode of the battery 913. The holding sleeve 914 is placed in the power source stem 91 and is used as part of the power source stem 91. The power source stem 91 also includes a permanent magnet 8 by which the power source stem connection member 911 will produce magnetic force such that the member 911 will be connected with the absorption stem connection member 5 through magnetic force absorption. In present embodiment, the permanent magnet 8 is an electromagnet and the shape thereof is consistent with the holding sleeve 910. The shape of the electromagnet is of a circular shape. A fixation hole 81 is defined in the middle portion of the permanent magnet 8. A power source stem insulation member 916 is disposed between the permanent magnet 8 and the first power source stem electrode 915. Protrusion bars 9121 for being pressed against the sleeve 910 and intake holes 9122 are provided on the base cover 912.

Figure 11:
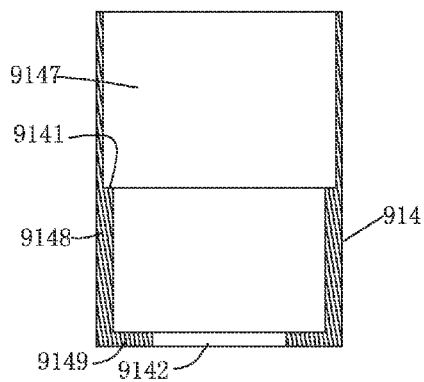
FIG. 11 shows a cross-sectional view of a holding sleeve of an electronic cigarette according to a first embodiment of the invention.

As shown in FIG. 11, the holding sleeve 914 is of a cylindrical cup shape and includes a side wall 9148, a bottom wall 9149 and a cavity 9147 defined by the side wall 9148 and bottom wall 9149. The holding sleeve 914 is pressed against and secured on the inner wall of the sleeve 910 by its side wall 9148. A locating step 9141 is formed on inner side of the inner wall 9148 of the holding sleeve for supporting the permanent magnet 8. The permanent magnet 8 is installed in the cavity of the holding sleeve 914 and the bottom of the permanent magnet 8 is supported on the locating step 9141. One end of the power source stem connection member and one end of the absorption stem connection member are inserted into the holding sleeve 914 and pressed against the top end of the permanent magnet 8 such that the permanent magnet 8 is held in place. A through hole 9142 is defined in the bottom wall 9149 of the holding sleeve. An insulation washer 918 is disposed between the first power source stem electrode 915 and holding sleeve 914. An axially extended venting hole is defined in the middle portion of the insulation washer 918. The lower portion of the first power source stem electrode 915 passes through the venting hole of the insulation washer 918 and through hole 9142 of the holding sleeve and then extends out of the bottom wall 9149 of the holding sleeve 914 for ventilation. The insulation washer 918 isolates the first power source stem electrode 915 from the holding sleeve 914. The holding sleeve 914 is a conductive member made of metal material, and it contacts the power source stem connection member 911 so as to conduct electricity.

Figure 10:
FIG. 10 shows a cross-sectional view of a power source stem connection member of an electronic cigarette according to a first embodiment of the invention.

Referring to FIG. 10, the power source stem connection member 911 matches the absorption stem connection member 5 and is made of magnetic material such as iron. The power source stem connection member 911 is disposed at the top end of the sleeve 910 for connecting the power source stem 91 and absorption stem 90. The power source stem connection member 911 is substantially of a hollow cylindrical shape and includes a first connection portion 9111 of cylinder in which a first cavity 9112 is formed for insertion with the lower portion 52 of the absorption stem connection member 5. A locating step 9113, which is radially outwardly extended from an outer wall of the first connection portion 9111 and used for engaging with the sleeve 910, is provided on the outer wall of the first connection portion 9111. The power source stem connection member 911 is pressed against and secured on the inner wall of the sleeve 914 by the outer wall of the first connection portion 9111 and is also pressed and secured on the inner wall of the sleeve 910 by the holding sleeve 914. The power source stem connection member 911 is used as the second power source stem electrode.

Referring to FIGS. 5 and 6, the first power source stem electrode 915 is substantially of a cylindrical shape. A circular locating step 9153 is formed on the middle circumferential surface of the first power source stem electrode 915 and said locating step 9153 divides the first power source stem electrode 915 into an upper portion 9151 and a lower portion 9152. In addition, an axially extended venting hole 9154 is defined in the first power source stem electrode. A power source stem insulation member 916 is sleeved on the upper portion 9151 of the first power source stem electrode and, they are inserted into the fixation hole 81 of the permanent magnet 8 and are locked therein. The bottom portion of the power source stem insulation member 916 is pressed against the top portion of the locating step 9153 such that the locating step 9153 of the first power source stem electrode is located below the bottom portion of the permanent magnet and the first power source stem electrode 915 is isolated from the permanent magnet 8.

A resilient member 917 is sleeved on the lower portion 9152 of the first power source stem electrode 915. In present embodiment, the resilient member is a spring. The two ends of the resilient member 917 are respectively pressed against the bottom surface of the locating step 9153 of the first power source stem electrode 915 and insulation washer 918. The first power source stem electrode 915, permanent magnet 8, power source stem connection member 911 and holding sleeve 914 are engaged each other tightly due to pre-tension generated by compression of the resilient member 917. In addition, the resilient member 917 makes the permanent magnet 8 being pressed more tightly against both of the power source stem connection member 911 and absorption stem connection member 5. By this manner, the first power source stem electrode 915 is always held and secured in the insulation ring 916 and no loosening occurs. The insulation washer 918 is capable of preventing short circuit between the first power source stem electrode 915 and holding sleeve 914. The resilient member 917 is pressed against the insulation washer 918 so as to prevent contact between the resilient member 917 and holding sleeve 914 which otherwise will result in electrical conduction.

During assembly of the electronic cigarette, the absorption stem connection member 5 is inserted into the power source stem connection member 911. Due to the existence of the permanent magnet 8, the absorption stem connection member 5 will be absorbed by the permanent magnet 8 and be pressed against the permanent magnet 8. Absorption force also exists between the power source stem connection member 911 and absorption stem connection member 5 and accordingly, tight connection between the absorption stem 90 and power source stem 91 is realized. When disassembling, what is needed is to overcome magnetic force so as to draw the absorption stem 90 out of the power source stem 91. This kind of connection leads to easiness and convenience in assembling and disassembling the electronic cigarette. Before the electronic cigarette is inserted and works, cigar liquid soaks and is storage into the fiber member 212 from the liquid storage component 37. During working process, the electrical circuit is switched on such that current flows across the electric heater coil 211 of the atomizer 21 and heat is generated. The cigar liquid stored in the fiber member 212 is heated and atomized by the electric heater coil 211 so that smoke is produced. The smoke passes through the guiding tube 35, then passes through the nozzle case 4 of the nozzle case venting hole 42 and finally be absorbed into mouth of the smoker.

Figure 12:
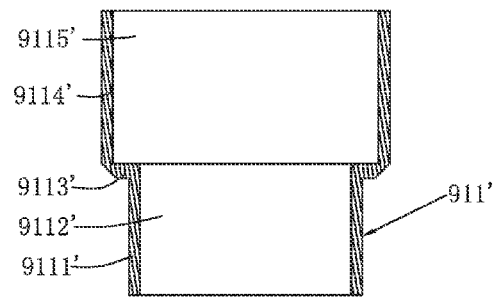
FIG. 12 shows a cross-sectional view of an absorption stem connection member of an electronic cigarette according to a second embodiment of the invention.
Figure 13:
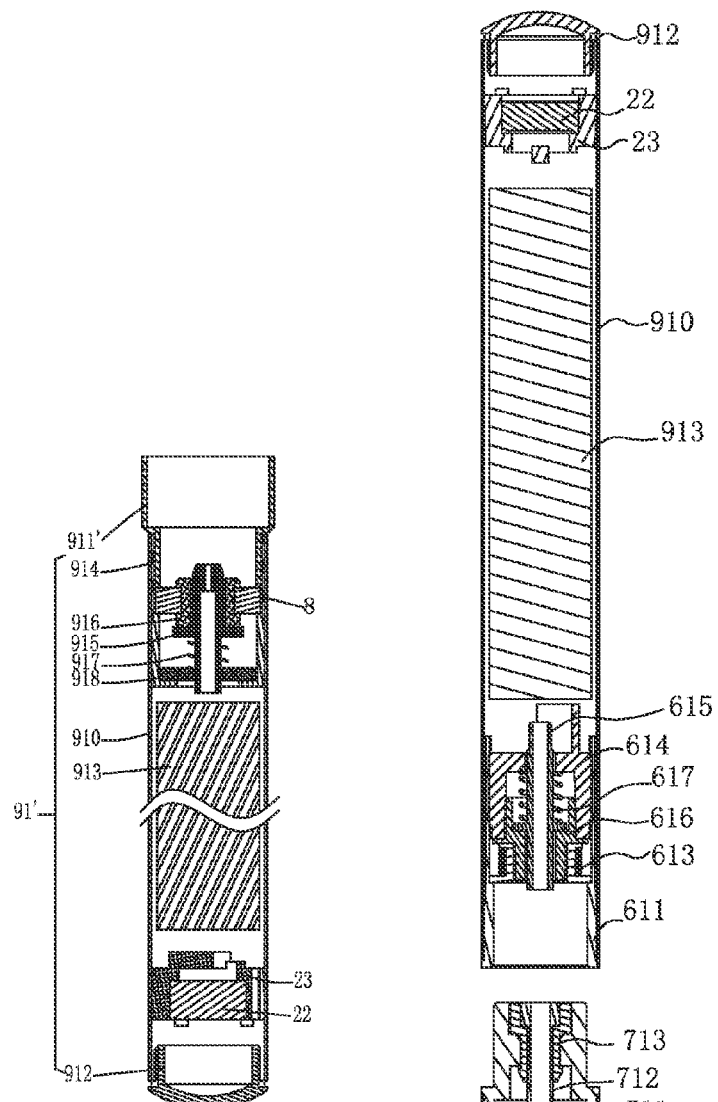
FIG. 13 shows a cross-sectional view of a power source stem connection member of an electronic cigarette according to a second embodiment of the invention.
Figure 14:
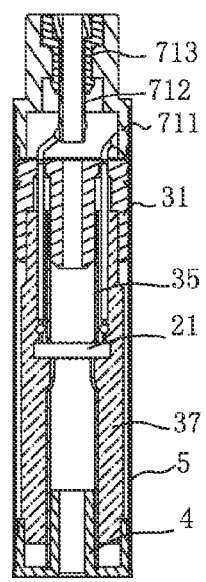
FIG. 14 shows a cross-sectional view of an electronic cigarette according to a third embodiment of the invention.

Referring to FIGS. 12 and 13 and according to a second embodiment of the invention, the power source stem 91' has similar construction to the power source stem 91 of the first embodiment and the difference lies in change of the power source stem connection member 911' of the power source stem 91'. The power source stem connection member 911' is substantially of a hollow cylindrical shape and includes a first connection portion 9111' of cylinder in which a first cavity 9112' is formed for insertion with the lower portion 52 of the absorption stem connection member 5. A locating step 9113', which is radially outwardly extended and used for engaging with the sleeve 910, is provided on the outer wall of the first connection portion 911'. The power source stem connection member 911' is pressed against and secured on the inner wall of the holding sleeve 914 by the outer wall of the first connection portion 9111'. Further, it is also pressed against and secured on the inner wall of the sleeve 910 by the holding sleeve 914. The power source stem connection member 911' further includes a second connection portion 9114' for engaging the absorption stem connection end. A cylinder is formed by extending axially away from the first connection portion 9111' from the locating step 9113' of the second connection portion 9114'. The first connection portion 9111' and second connection portion 9114' are communicated with each other. A second cavity 9115' is defined in the second connection portion 9114' for receiving the absorption stem connection end (the second end 12 of the absorption sleeve of the absorption stem). The inner wall of the second connection portion 9114' is interference-fitted with the outer wall of the absorption stem connection end such that the connection between the absorption stem 90 and power source stem 91 becomes more reliable.

Though various embodiments have been described, the scope of the invention is not limited to them. The permanent magnet 8 may be disposed in the power source stem 91. Understandingly, the permanent magnet 8 may also be disposed in the absorption stem 90. The first absorption stem electrode 13 is inserted into the fixation hole of the permanent magnet. An insulation member is disposed between the permanent magnet and first absorption stem electrode. The absorption stem connection member is the second absorption stem electrode. The power source stem connection member is the second power source stem electrode. The first power source stem electrode is provided in the power source stem connection member. An insulation member is disposed between the first and second power source stem electrodes. The present invention may also be embodied as follows. Both of the absorption stem 90 and power source stem 91 are provided with a permanent magnet 8. When connecting the absorption stem connection member and power source stem connection member, the permanent magnets 8 thereof are attracted with each other. The substantial structure of this embodiment is consistent with that of the above embodiment and therefore, no further description will be provided hereinafter.

Referring to FIGS. 14-26, as an alternative embodiment, in a third embodiment, an electromagnetic coil assembly 613 is employed to replace the permanent magnet. The absorption stem connection member 711 and power source stem connection member 611 are attracted together and are pressed against the top end of the electromagnetic coil assembly 613. In this embodiment, the electromagnetic coil assembly 613 is held in the power source stem connection member 611 via a base 614.

Figure 23:
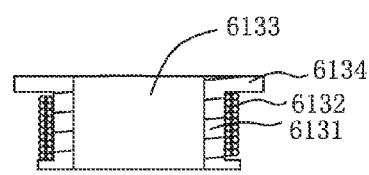
FIG. 23 shows a cross-sectional view of an electromagnetic coil assembly of an electronic cigarette according to a third embodiment of the invention.
Figure 24:
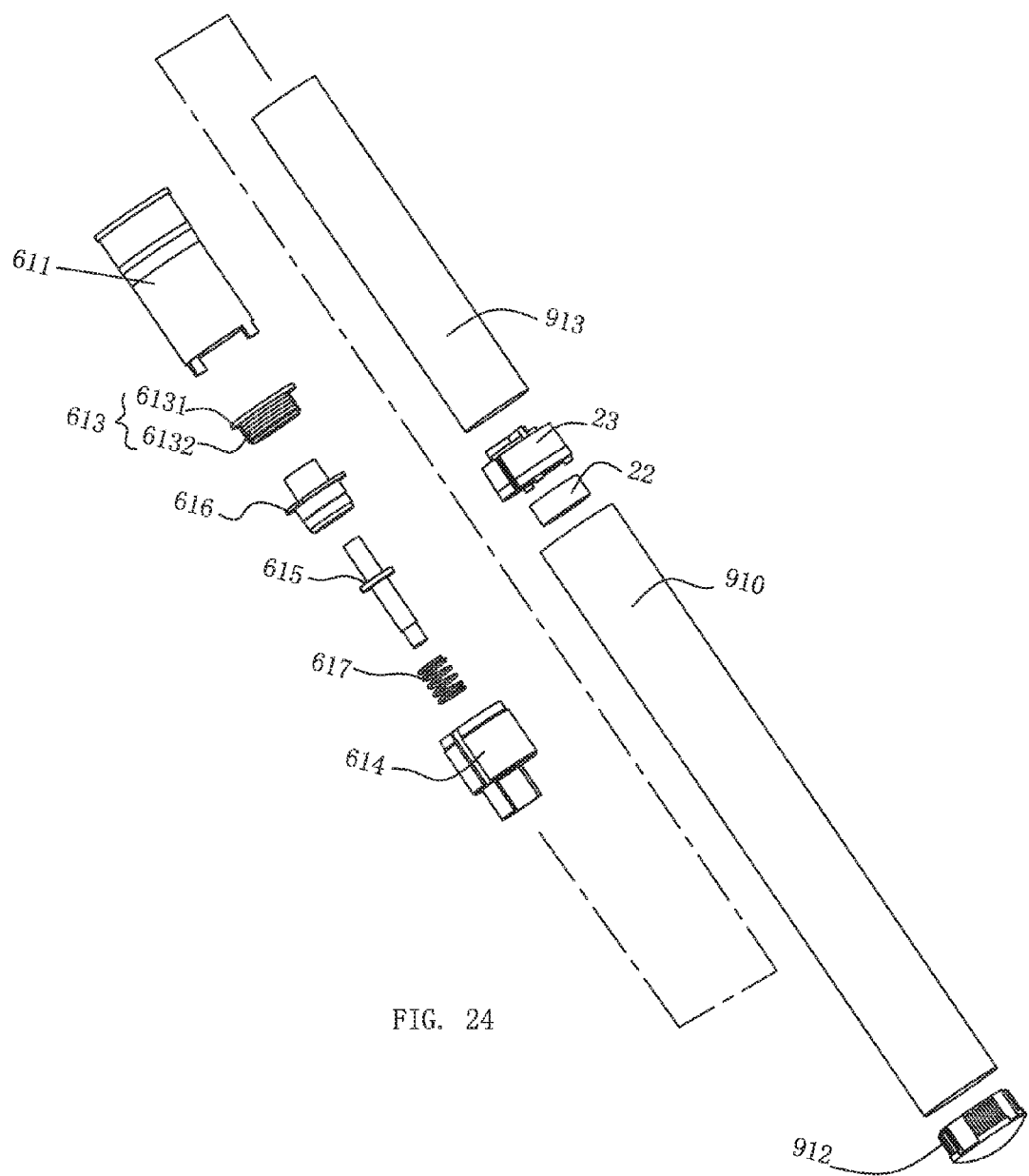
FIG. 24 shows an exploded view of a power source stem of an electronic cigarette according to a third embodiment of the invention.
Figure 25:
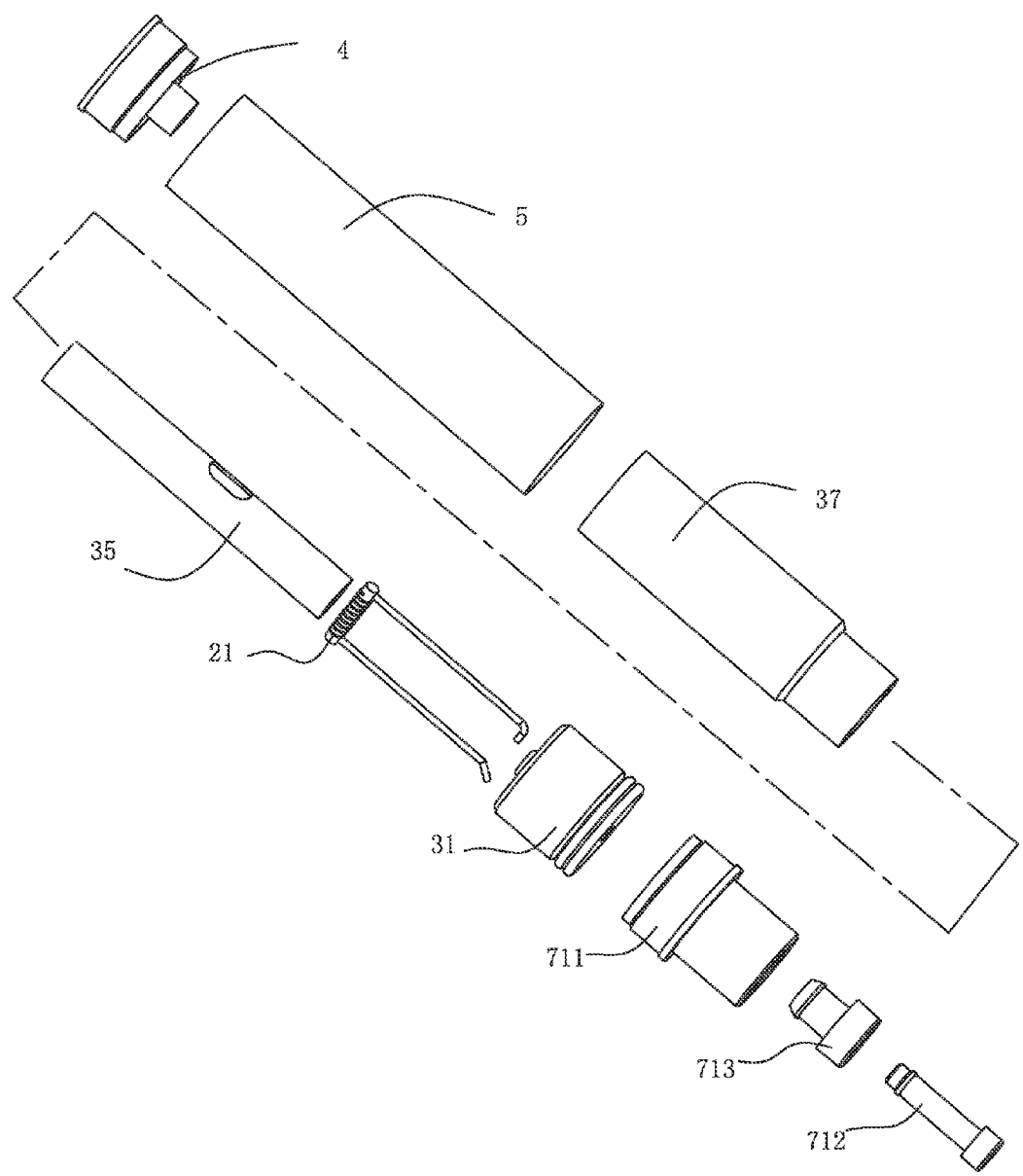
FIG. 25 shows an exploded view of an absorption stem of an electronic cigarette according to a third embodiment of the invention.

Referring to FIGS. 23-24, the electromagnetic coil assembly 613 includes a magnetic core 6131 and a coil 6132 enwound on the magnetic core. A through hole 6133 is defined in the magnetic core 6131. A groove (not shown) is defined in the outer wall of the magnetic core 6131 for enwinding the coil thereon. A radially extended locating step 6134 is defined in the upper end of the magnetic core 6131. The first power source stem electrode 615 is inserted into the through hole 6133 of the magnetic core. An insulation sleeve 616 is located between the magnetic core 6133 and first power source stem electrode 615. The power source stem connection member 611 is used as the second power source stem electrode. The coil 6132 may be made of copper. The magnetic core may be formed by soft magnetic material such as any one or more of pure iron and soft steel, Fe—Si material, Fe—Al type material, Fe—Si—Al type material, Fe—Ni type material, Fe—Co type material, soft ferrite material, amorphous soft magnetic material, and nana-crystalline soft magnetic material.

Figure 20:
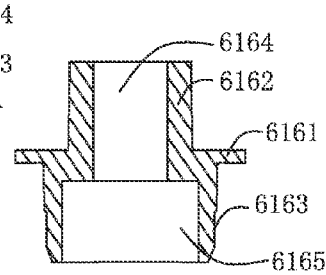
FIG. 20 shows a cross-sectional view of an insulation sleeve of an electronic cigarette according to a third embodiment of the invention.

Referring to FIG. 20, the insulation sleeve 616 is of a cylindrical shape. A circular locating step 6161 is formed on the middle circumferential surface of the insulation sleeve 616 and said locating step divides the insulation sleeve 616 into an upper portion 6162 and a lower portion 6163. In addition, an axially extended venting hole 6164 is defined in the insulation sleeve 616. A receiving chamber 6165 is defined in the lower portion of the insulation sleeve. The first power source stem electrode 615 is inserted into the through hole 6164 of the insulation sleeve. The locating step 6161 of the insulation sleeve is located between the electromagnetic coil assemble 613 and base 614 and isolates them from each other.

Figure 21:
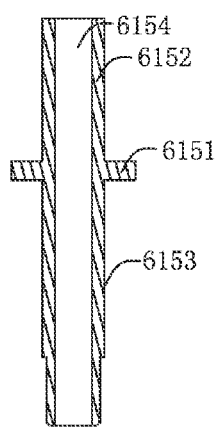
FIG. 21 shows a cross-sectional view of a first power source stem electrode of an electronic cigarette according to a third embodiment of the invention.

Referring to FIG. 21, the first power source stem electrode 615 is of a cylindrical shape. A circular locating step 6151 is formed on the middle circumferential surface of the first power source stem electrode and said locating step 6151 divides the first power source stem electrode into an upper portion 6152 and a lower portion 6153. In addition, an axially extended venting hole 6151 is defined in the first power source stem electrode 615. The insulation member 616 is sleeved on the upper portion 6152 of the first power source stem electrode and, the first power source stem electrode and insulation member are inserted into the through hole 6133 of the electromagnetic coil assembly and are locked therein. The lower portion 6153 of the first power source stem electrode is received into the receiving chamber 6165 of the lower portion 6163 of the insulation sleeve. The locating step 6151 of the first power source stem electrode is pressed against the bottom end of the upper portion 6162 of the insulation sleeve.

Figure 19:
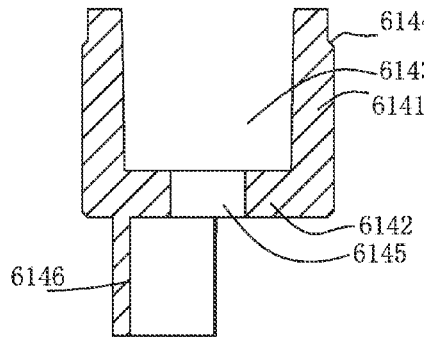
FIG. 19 shows a cross-sectional view of a base of an electronic cigarette according to a third embodiment of the invention.

Referring to FIG. 19, the base 614 is of a circular cup and includes a side wall 6141, a bottom wall 6142 and a cavity 6143 defined by the side wall and bottom wall together. The base 614 is pressed against and secured on an inner wall of the power source stem connection end by its side wall 6141. A locating step 6144 is inwardly formed on the upper end of the side wall 6141 of the base 614. A through hole 6145 is defined in the bottom wall of the base 614 through which the first power source stem electrode 615 passes. An axially extended semi-circular stopping wall 6146 is formed on the bottom wall of the base 614 around the through hole 6145. The stopping wall separates an electric wire for connecting with the first power source stem electrode 615 from another electric wire for connecting with the power source stem connection member 611.

Figure 15:
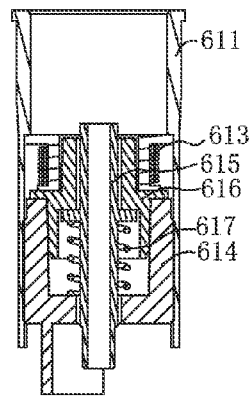
FIG. 15 shows an assembled cross-sectional view of a magnetic force connection head component of an electronic cigarette according to a third embodiment of the invention.
Figure 16:
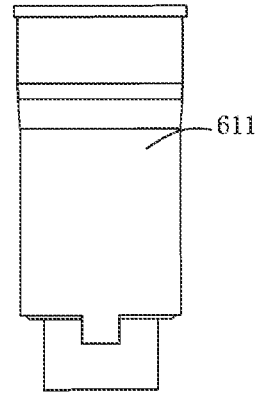
FIG. 16 shows a front view of a magnetic force connection head component of an electronic cigarette according to a third embodiment of the invention.

Referring to FIG. 15, a spring 617 is sleeved on the lower portion 6153 of the first power source stem electrode. The two ends of the spring 617 are respectively pressed against the locating step 6151 of the first power source stem electrode and inner side of the bottom wall 6142 of the base. The first power source stem electrode 615, electromagnetic coil assembly 613, power source stem connection member 611 and base 614 are engaged each other tightly due to pre-tension generated by compression of the spring 617. In addition, the spring 617 makes the electromagnetic coil assembly 613 be pressed more tightly against both of the power source stem connection member 611 and absorption stem connection member 711, thus leading to more stable connection structure, tighter physical and electrical contact between the first power source stem electrode 615 and the first absorption stem electrode.

Figure 17:
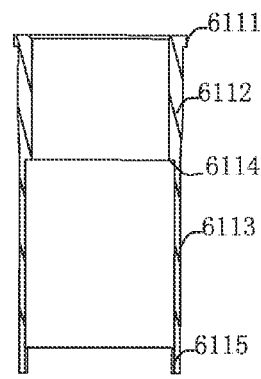
FIG. 17 shows a cross-sectional view of a power source stem connection member of an electronic cigarette according to a third embodiment of the invention.

Referring to FIG. 17, the power source stem connection member 611 is of a cylindrical shape and, a locating step 6111 extended radially outwardly is formed on the upper end thereof for engaging the power source stem connection end. The side wall of the power source stem connection member 611 is divided into an upper portion 6112 for receiving the absorption stem connection member 711 and a lower portion 6113 for receiving the electromagnetic coil assembly 613, the first power source stem electrode 615 and base 614. The transition location between the upper portion and lower portion of the side wall of the power source stem connection member is provided with a step 6114 against which the upper end surface of the magnetic core 6131 of the electromagnetic coil assembly is pressed. The outer diameter of the upper portion 6112 of the side wall of the power source stem connection member becomes gradually greater such that the power source stem connection member 611 is secured into the inner wall of the power source stem connection end. The lower end of the power source stem connection member is provided with two wiring pins 6115 for wiring.

Figure 18:
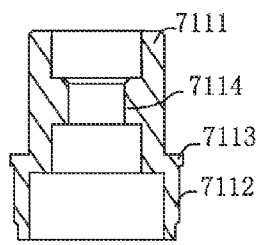
FIG. 18 shows a cross-sectional view of an absorption stem connection member of an electronic cigarette according to a third embodiment of the invention.

Referring to FIG. 18, the absorption stem connection member 711 includes an upper portion 7111 and a lower portion 7112 both of which are of a cylindrical shape. The upper portion 7111 is intended for connection with the absorption stem connection end, whereas the lower portion 7112 is intended for connection with the power source stem connection member 611. A locating step 7113, which is extended outwardly and is pressed against the absorption stem connection end, is formed between the upper and power portions 7111 and 7112. The locating step also functions to be pressed against the power source stem connection member so as to realize location limiting purpose. A locking ring 7114 for mounting the first absorption stem electrode 712 is formed on the inner wall of the lower portion 7112. The first absorption stem electrode 712 is secured in the locking ring 7114 by an insulation ring 713. An axially extended venting hole is defined in the middle portion of the first absorption stem electrode 712.

Figure 22:
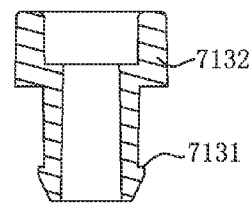
FIG. 22 shows a cross-sectional view of an insulation ring of an electronic cigarette according to a third embodiment of the invention.

Referring to FIG. 22, the insulation ring 713 is disposed between the first absorption stem electrode 712 and locking ring 7114 of the absorption stem connection member. One end of the insulation ring 713 is provided with inverted rim 7131 to be located at one side of the locking ring 7114, while the other end thereof is provided with a radially extended cylindrical boss 7132 to be located at the other side of the locking ring 7114, hereby the insulation ring 713 being just locked in the locking ring 7114 of the absorption stem connection member.

Figures 26, 27:
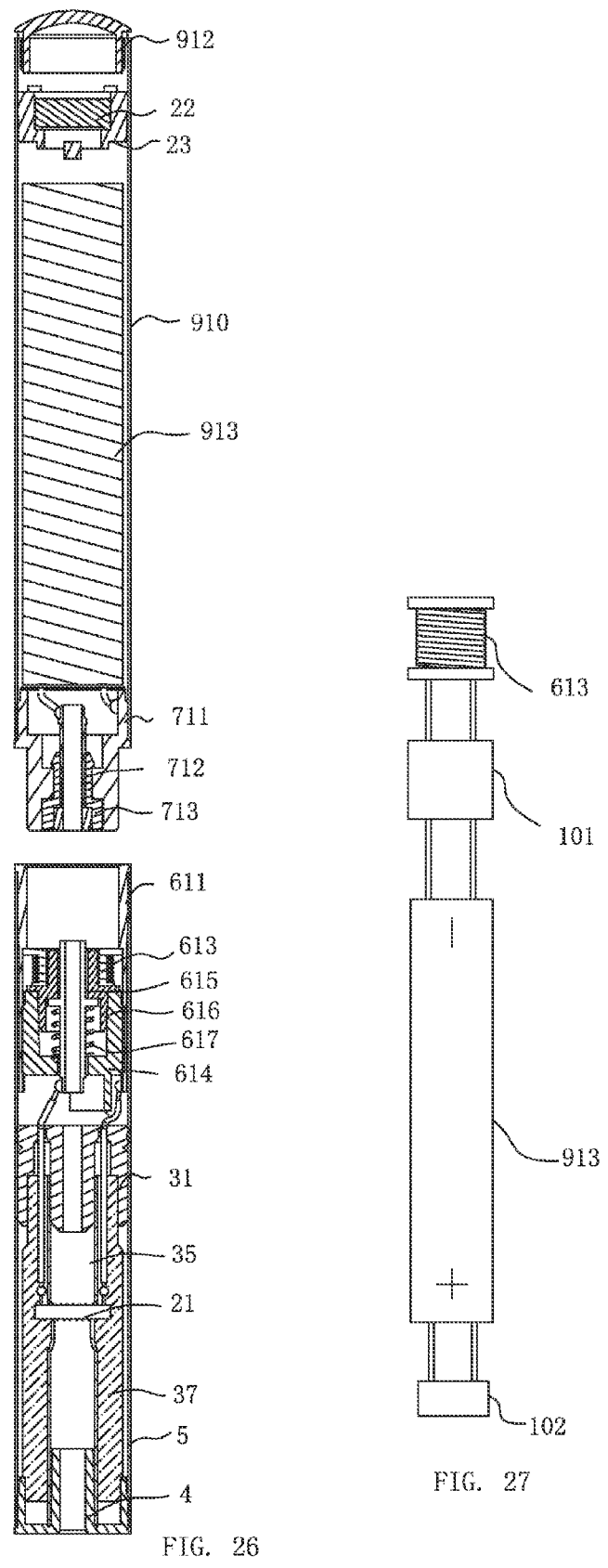
FIG. 26 shows a cross-sectional view of an electronic cigarette according to a fourth embodiment of the invention.
FIG. 27 illustrates working principle of the electromagnet of the invention.

Referring to FIG. 26, the difference between the fourth embodiment and third embodiment is described as follows. The electromagnetic coil assembly 613 is disposed in the absorption stem connection end and, the electrode construction inside the absorption stem is exchanged with the electrode construction inside the power source stem. The substantial features of this embodiment are consistent with those of the above-mentioned embodiment and therefore, no further description will be provided hereinafter.

Referring to FIG. 27 illustrating work principle of the electromagnetic coil assembly 613 of the invention, the electromagnetic coil assembly 613 may be powered by the electronic cigarette battery 913 or by a separate battery. A sensor 102 disposed in the electronic cigarette acquires relevant information and then commands the controller 101 to control working status of the electromagnetic coil assembly 613. The information sensed by the sensor 102 may be set according to requirement such as voltage change of the battery, circuit current change, switch off or switch on of the circuit. Or, it may be based on forces applied or whether insertion or pulling out of the magnetic force absorption component is sensed. Based on the information sensed by the sensor 102, the controller 101 controls the battery 913 so that the battery 913 will supply or cut off the power, thus controlling whether the electromagnetic coil assembly 613 will produce magnetic force, and finally making the absorption stem 90 and power source stem 91 be connected with each other by magnetic force absorption.

Though various embodiments of the invention have been illustrated above, a person of ordinary skill in the art will understand that, variations and improvements made upon the illustrative embodiments fall within the scope of the invention, and the scope of the invention is only limited by the accompanying claims and their equivalents.

What is claimed is:

1. An electronic cigarette comprising an absorption stem and a power source stem; the absorption stem has a first and second absorption stem electrodes contained therein; the power source stem has a first and second power source stem electrodes contained therein; when the absorption stem and power source stem are connected with each other, the first absorption stem electrode is electrically connected to the first power source stem electrode, while the second absorption stem electrode is electrically connected to the second power source stem electrode, wherein the absorption stem and power source stem are connected together by magnetic force absorption;

a magnetic absorption element is disposed in at least one of the connection end of the absorption stem and connection end of the power source stem engaged with the connection end of the absorption stem; the connection end of the absorption stem is provided with a metal absorption stem connection member, while the connection end of the power source stem is provided with a metal power source stem connection member; the absorption stem connection member and power source stem connection member are detachably connected with each other, and they are engaged with each other by absorption force of the magnetic absorption element;

the magnetic absorption element is a permanent magnet; the absorption stem connection member and power source stem connection member are attracted together and are pressed against the top end of the permanent magnet; or, the magnetic absorption element is an electromagnetic coil assembly; the absorption stem connection member and power source stem connection member are attracted together and are pressed against the top end of the electromagnetic coil assembly; the permanent magnet is held in the absorption stem connection end or power source stem connection end by a metal holding sleeve;

the permanent magnet is disposed on the power source stem connection end and a fixation hole is defined in the permanent magnet; the first power source stem electrode is received in the fixation hole of the permanent magnet; an insulation member is disposed between the permanent magnet and the first power source stem electrode; the power source stem connection member is the second power source stem electrode, and the absorption stem connection member is the second absorption stem electrode; the first absorption stem electrode is placed in the absorption stem connection member; an insulation member is disposed between the first and second absorption stem electrodes.

2. The electronic cigarette as recited in claim 1, wherein the holding sleeve is of a circular cup and includes a side wall, a bottom wall and a cavity defined by the side wall and bottom wall together; the holding sleeve is pressed against and secured on an inner wall of the power source stem connection end by its side wall; a locating step is formed on inner side of the inner wall of the holding sleeve for supporting the permanent magnet; the permanent magnet is installed in the cavity of the holding sleeve and the bottom of the permanent magnet is supported on the locating step; one end of the power source stem connection member and one end of the absorption stem connection member are inserted into the holding sleeve and pressed against the top end of the permanent magnet such that the permanent magnet is held in place; a through hole is defined in the bottom wall of the holding sleeve.

3. The electronic cigarette as recited in claim 2, wherein the power source stem connection member is pressed against and secured on the power source stem connection end by the holding sleeve and, the holding sleeve is pressed against and secured on the inner wall of the power source stem connection end; the permanent magnet is held in the holding sleeve.

4. The electronic cigarette as recited in claim 2, wherein the power source stem connection member includes a first connection portion of cylinder in which a first cavity is formed for insertion with the absorption stem connection member; a locating step, which is radially outwardly extended and used for engaging with the power source stem connection end, is provided on the outer wall of the first connection portion; the power source stem connection member is pressed against and secured on the inner wall of the power source stem connection end by the outer wall of the first connection portion.

5. The electronic cigarette as recited in claim 4, wherein the power source stem connection member further includes a second connection portion for insertion with the absorption stem connection end; the second connection portion extends axially upon the locating step away from the first connection portion such that a cylinder is formed; the first and second connection portions communicate with each other; a second cavity is defined in the second connection portion for containing the absorption stem connection end; the inner wall of the second connection portion is interference-fitted with the outer wall of the absorption stem connection end.

6. The electronic cigarette as recited in claim 1, wherein the absorption stem connection member includes an upper portion and a lower portion both of which are of a cylindrical shape; the upper portion is intended for connection with the absorption stem connection end, whereas the lower portion is intended for connection with the power source stem connection member; a locating step, which is extended outwardly and is pressed against the absorption stem connection end, is formed between the upper and power portions; the locating step also functions to be pressed against the power source stem connection member so as to realize location limiting purpose; a locking ring for mounting the first absorption stem electrode is formed on the inner wall of the lower portion; the first absorption stem electrode is secured in the locking ring by an insulation member; a venting hole is defined in the middle portion of the first absorption stem electrode.

7. The electronic cigarette as recited in claim 2, wherein the first power source stem electrode is of a cylindrical shape; a circular locating step is formed on the middle circumferential surface of the first power source stem electrode and said locating step divides the first power source stem electrode into an upper portion and a lower portion; an axially extended venting hole is defined in the first power source stem electrode; the insulation member is sleeved on the first power source stem electrode and, the first power source stem electrode and insulation member are inserted into the fixation hole of the permanent magnet and are locked therein; the bottom portion of the insulation member is pressed against the top portion of the locating step such that the locating step of the first power source stem electrode is located below the bottom portion of the permanent magnet and is isolated from the permanent magnet.

8. The electronic cigarette as recited in claim 7, wherein an insulation washer is disposed between the first power source stem electrode and holding sleeve; an axially extended venting hole is defined in the middle portion of the insulation washer; a resilient member is sleeved on the outer wall of the lower portion of the first power source stem electrode; the two ends of the resilient member are respectively pressed against the locating step of the first power source stem electrode and insulation washer; the first power source stem electrode, permanent magnet, power source stem connection member and holding sleeve are engaged each other tightly due to pre-tension generated by compression of the resilient member;

the resilient member makes the permanent magnet be pressed tightly against both of the power source stem connection member and absorption stem connection member.

9. The electronic cigarette as recited in claim 8, wherein the lower portion of the first power source stem electrode passes through the venting hole of the insulation washer and through hole of the holding sleeve and then extends out of the bottom wall of the holding sleeve.

10. An electronic cigarette comprising an absorption stem and a power source stem; the absorption stem has a first and second absorption stem electrodes contained therein; the power source stem has a first and second power source stem electrodes contained therein; when the absorption stem and power source stem are connected with each other, the first absorption stem electrode is electrically connected to the first power source stem electrode, while the second absorption stem electrode is electrically connected to the second power source stem electrode, wherein the absorption stem and power source stem are connected together by magnetic force absorption;

a magnetic absorption element is disposed in at least one of the connection end of the absorption stem and connection end of the power source stem engaged with the connection end of the absorption stem; the connection end of the absorption stem is provided with a metal absorption stem connection member, while the connection end of the power source stem is provided with a metal power source stem connection member; the absorption stem connection member and power source stem connection member are detachably connected with each other, and they are engaged with each other by absorption force of the magnetic absorption element;

the magnetic absorption element is a permanent magnet; the absorption stem connection member and power source stem connection member are attracted together and are pressed against the top end of the permanent magnet; or, the magnetic absorption element is an electromagnetic coil assembly; the absorption stem connection member and power source stem connection member are attracted together and are pressed against the top end of the electromagnetic coil assembly; the permanent magnet is held in the absorption stem connection end or power source stem connection end by a metal holding sleeve;

a fixation hole is defined in the permanent magnet which is disposed at the absorption stem connection end; the first absorption stem electrode is received in the fixation hole of the permanent magnet; an insulation member is disposed between the permanent magnet and the first absorption stem electrode; the absorption stem connection member is the second absorption stem electrode, and the power source stem connection member is the second power source stem electrode; the first power source stem electrode is placed in the power source stem connection member; an insulation member is disposed between the first and second power source stem electrodes.

11. An electronic cigarette comprising an absorption stem and a power source stem; the absorption stem has a first and second absorption stem electrodes contained therein; the power source stem has a first and second power source stem electrodes contained therein; when the absorption stem and power source stem are connected with each other, the first absorption stem electrode is electrically connected to the first power source stem electrode, while the second absorption stem electrode is electrically connected to the second power source stem electrode, wherein the absorption stem and power source stem are connected together by magnetic force absorption;

a magnetic absorption element is disposed in at least one of the connection end of the absorption stem and connection end of the power source stem engaged with the connection end of the absorption stem; the connection end of the absorption stem is provided with a metal absorption stem connection member, while the connection end of the power source stem is provided with a metal power source stem connection member; the absorption stem connection member and power source stem connection member are detachably connected with each other, and they are engaged with each other by absorption force of the magnetic absorption element;

the magnetic absorption element is a permanent magnet; the absorption stem connection member and power source stem connection member are attracted together and are pressed against the top end of the permanent magnet; or, the magnetic absorption element is an electromagnetic coil assembly; the absorption stem connection member and power source stem connection member are attracted together and are pressed against the top end of the electromagnetic coil assembly; the permanent magnet is held in the absorption stem connection end or power source stem connection end by a metal holding sleeve;

the electromagnetic coil assembly is secured in the absorption stem connection end or power source stem connection end by a base; the electromagnetic coil assembly includes a magnetic core and a coil enwound on the magnetic core; a through hole is defined in the magnetic core; a groove is defined in the outer wall of the magnetic core for enwinding the coil thereon; a radially extended locating step is defined in the upper end of the magnetic core; the first power source stem electrode is inserted into the through hole of the magnetic core; an insulation sleeve is located between the magnetic core and first power source stem electrode; the power source stem connection member is used as the second power source stem electrode.

12. The electronic cigarette as recited in claim 11, wherein the insulation sleeve is of a cylindrical shape; a circular locating step is formed on the middle circumferential surface of the insulation sleeve and said locating step divides the insulation sleeve into an upper portion and a lower portion; an axially extended venting hole is defined in the insulation sleeve; a receiving chamber is defined in the lower portion of the insulation sleeve for communicating with the through hole; the first power source stem electrode is inserted into the through hole of the insulation sleeve; the locating step of the insulation sleeve is located between the electromagnetic coil assemble and base.

13. The electronic cigarette as recited in claim 12, wherein the first power source stem electrode is of a cylindrical shape; a circular locating step is formed on the middle circumferential surface of the first power source stem electrode and said locating step divides the first power source stem electrode into an upper portion and a lower portion; an axially extended venting hole is defined in the first power source stem electrode; the insulation sleeve is sleeved on the upper portion of the first power source stem electrode and, the first power source stem electrode and insulation sleeve are inserted into the through hole of the electromagnetic coil assembly and are locked therein; the lower portion of the first power source stem electrode is received into the receiving chamber of the lower portion of the insulation sleeve; the locating step of the first power source stem electrode is pressed against the bottom end of the upper portion of the insulation sleeve; the holding sleeve is of a circular cup and includes a side wall, a bottom wall and a cavity defined by the side wall and bottom wall together; the holding sleeve is pressed against and secured on an inner wall of the power source stem connection end by its side wall; a locating step is formed on inner side of the inner wall of the holding sleeve; a through hole is defined in the bottom wall of the holding sleeve; the lower portion of the first power source stem electrode passes through said through hole.

14. The electronic cigarette as recited in claim 13, wherein an axially extended semi-circular stopping wall is formed on the bottom wall of the base around the through hole; a resilient member is sleeved on the lower portion of the first power source stem electrode; the two ends of the resilient member are respectively pressed against the locating step of the first power source stem electrode and inner side of the bottom wall of the holding sleeve.

15. The electronic cigarette as recited in claim 11, wherein the power source stem connection member is of a cylindrical shape and, a locating step extended radially outwardly is formed on the upper end thereof for engaging the power source stem connection end; the side wall of the power source stem connection member is divided into an upper portion for receiving the absorption stem connection member and a lower portion for receiving the electromagnetic coil assembly, the first power source stem electrode and holding sleeve; the transition location between the upper portion and lower portion of the side wall of the power source stem connection member is provided with a step against which the upper end surface of the magnetic core of the electromagnetic coil assembly is pressed; the outer diameter of the upper portion of the side wall of the power source stem connection member becomes gradually greater such that the power source stem connection member is secured into the inner wall of the power source stem connection end; the lower end of the power source stem connection member is provided with two wiring pins.

16. The electronic cigarette as recited in claim 11, wherein the absorption stem connection member includes an upper portion and a lower portion both of which are of a cylindrical shape; the upper portion is intended for connection with the absorption stem connection end, whereas the lower portion is intended for connection with the power source stem connection member; a locating step, which is extended radially outwardly and is pressed against the absorption stem connection end, is formed between the upper and power portions; the locating step also functions to be pressed against the power source stem connection member so as to realize location limiting purpose; a locking ring for mounting the first absorption stem electrode is formed on the inner wall of the lower portion; the first absorption stem electrode is secured in the locking ring by an insulation member; a venting hole is defined in the middle portion of the first absorption stem electrode; the insulation ring is disposed between the first absorption stem electrode and locking ring of the absorption stem connection member; one end of the insulation ring is provided with an inverted rim to be located at one side of the locking ring, while the other end thereof is provided with a radially extended cylindrical boss to be located at the other side of the locking ring.

17. The electronic cigarette as recited in claim 11, wherein the electromagnetic coil assembly includes a magnetic core and a coil enwound on the magnetic core; a through hole is defined in the magnetic core; a groove is defined in the outer wall of the magnetic core for enwinding the coil thereon; a radially extended locating step is defined in the upper end of the magnetic core; the first absorption stem electrode is inserted into the through hole of the magnetic core; an insulation sleeve is located between the magnetic core and first absorption stem electrode; the absorption stem connection member is used as the second absorption stem electrode.

* * * * *